United States Patent
Lacey (10) Patent No.: US 9,044,151 B2
(45) Date of Patent: Jun. 2, 2015

(54) STRADDLE MOUNT DETECTOR ASSEMBLY

(71) Applicant: General Electric Company, Schenectady, NY (US)

(72) Inventor: Joseph Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 104 days.

(21) Appl. No.: 13/916,123

(22) Filed: Jun. 12, 2013

(65) Prior Publication Data

US 2014/0369462 A1    Dec. 18, 2014

(51) Int. Cl.
*A61B 6/00* (2006.01)
*A61B 6/03* (2006.01)

(52) U.S. Cl.
CPC .......... *A61B 6/03* (2013.01); *A61B 6/4266* (2013.01); *A61B 6/4429* (2013.01); *Y10T 29/49002* (2015.01); *A61B 6/035* (2013.01); *A61B 6/4233* (2013.01); *A61B 6/4435* (2013.01); *A61B 6/482* (2013.01)

(58) Field of Classification Search
CPC .......... A61B 6/00; A61B 6/03; A61B 6/032; G01N 23/046

USPC .............................................. 378/4–20
See application file for complete search history.

(56) References Cited

U.S. PATENT DOCUMENTS

| 4,799,245 | A | 1/1989 | Bernardi |
| 6,337,894 | B1 | 1/2002 | Tybinkowski et al. |
| 8,308,361 | B2 | 11/2012 | Gregerson et al. |
| 2004/0120448 | A1 | 6/2004 | Ratzmann |
| 2011/0058644 | A1* | 3/2011 | Thran et al. ............ 378/11 |

OTHER PUBLICATIONS

Search Report and Written Opinion from corresponding PCT Application No. PCT/US2014/041642 dated Aug. 28, 2014.

* cited by examiner

*Primary Examiner* — Courtney Thomas
(74) *Attorney, Agent, or Firm* — Lucas Divine; General Electric Company (57) ABSTRACT

A CT system includes a gantry having a rotatable base and having an opening for receiving an object to be scanned, and a detector assembly. The detector assembly includes a plurality of detectors positioned to receive x-rays having passed through the object, and an arcuate structure positioned to support the plurality of detectors. A first support frame is attached to the rotatable base at a first axial location and supported at a second axial location, wherein the arcuate structure is attached to the first support frame between the first axial location and the second axial location.

17 Claims, 5 Drawing Sheets

STRADDLE MOUNT DETECTOR ASSEMBLY

BACKGROUND

This disclosure relates generally to diagnostic imaging and, more particularly, to an improved support structure for a computed tomography (CT) detector assembly.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

The detector array (or assembly) and the x-ray tube are structurally mounted to the gantry. Generally, the detector is mounted in a cantilever fashion to a structural plate or integrated onto a vertical surface. That is, the rotating base of the gantry typically rotates about a patient or z-axis of the CT system, and the detector assembly is mounted axially therefrom (extending from the rotating base along the z-axis).

Such a mounting scheme has proven adequate to support the detector assembly and, although cantilever mounted, the amount of deflection has not been excessive. However, in recent years at least two changes in system design have caused an increased propensity for cantilever-mounted detector designs to deflect to unacceptable levels. First, gantry rotational speeds have increased and some image acquisitions are performed at gantry speeds of five revolutions/second or greater. Second, detector coverage in the z-direction has also increased and detectors having greater than 64 slices have been implemented. The increased length in z corresponds to a yet larger cantilever loading of the detector. As such, speed-dependent artifacts may be experienced due to this combined effect of increased cantilever loading and increased gantry speed.

In addition, as the axial length of the detector (in z) has increased, so too has the location for mounting the x-ray tube. That is, typically the x-ray tube is mounted on the gantry and on the rotating base such that its focal spot is centered axially approximately on the centermost detector in z. However, as the detectors increase in length, the x-ray tube itself is also moved axially and in accordance with the central z detector. Thus, the propensity for speed-dependent artifacts is compounded yet further, as the x-ray tube may also be supported using a longer cantilever arm, as well, which may also noticeably deflect during high speed gantry operation.

Therefore, it would be desirable to have a method and apparatus to improve mounting of components of a CT system on a gantry.

BRIEF DESCRIPTION

Embodiments are directed toward a method and apparatus to improve mounting of components of a CT system on a gantry.

According to one aspect, a CT system includes a gantry having a rotatable base and having an opening for receiving an object to be scanned, and a detector assembly. The detector assembly includes a plurality of detectors positioned to receive x-rays having passed through the object, and an arcuate structure positioned to support the plurality of detectors. A first support frame is attached to the rotatable base at a first axial location and supported at a second axial location, wherein the arcuate structure is attached to the first support frame between the first axial location and the second axial location.

According to another aspect, a method of assembling a CT system includes coupling a rotatable base to a gantry, the gantry having an opening for receiving an object to be scanned, attaching an arc-shaped structure to the rotatable base via a first support frame such that the arc-shaped structure is supported at a first axial location and a second axial location, and positioning a plurality of detectors on a surface of the arc-shaped structure to receive x-rays that pass through the opening and through the object.

According to yet another aspect, a detector assembly for a CT imaging system includes an arced structure having a plurality of detectors positioned thereon, wherein the assembly is attachable to a rotatable base of the CT system such that x-rays generated in the imaging system impinge upon the plurality of detectors after having passed through an object to be imaged, and a first support frame that axially straddles the arced structure and supports the arced surface at a first axial location and a second axial location.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that embodiments are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
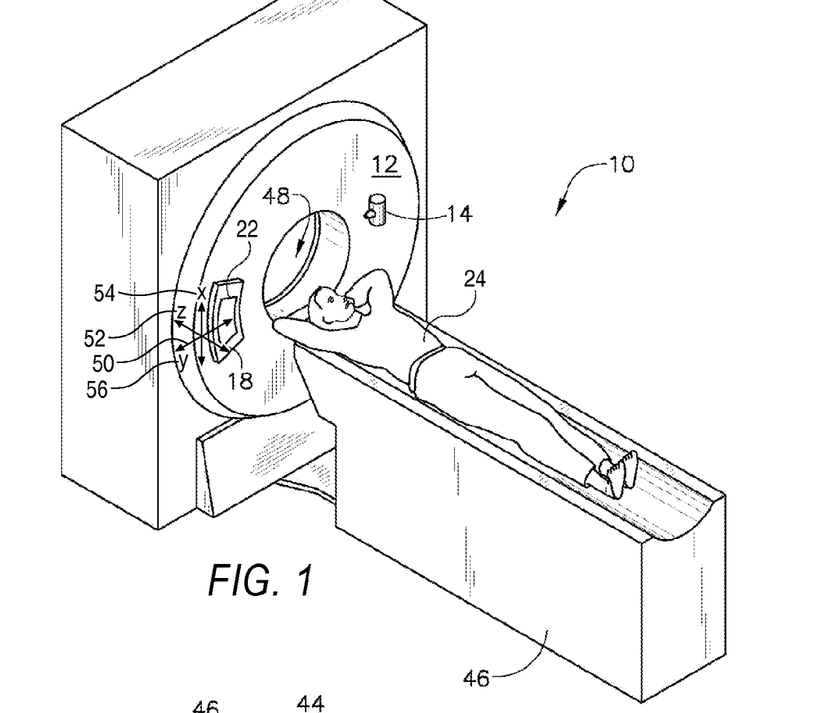
FIG. 1 is a pictorial view of a CT imaging system that incorporates disclosed embodiments.
Figure 2:
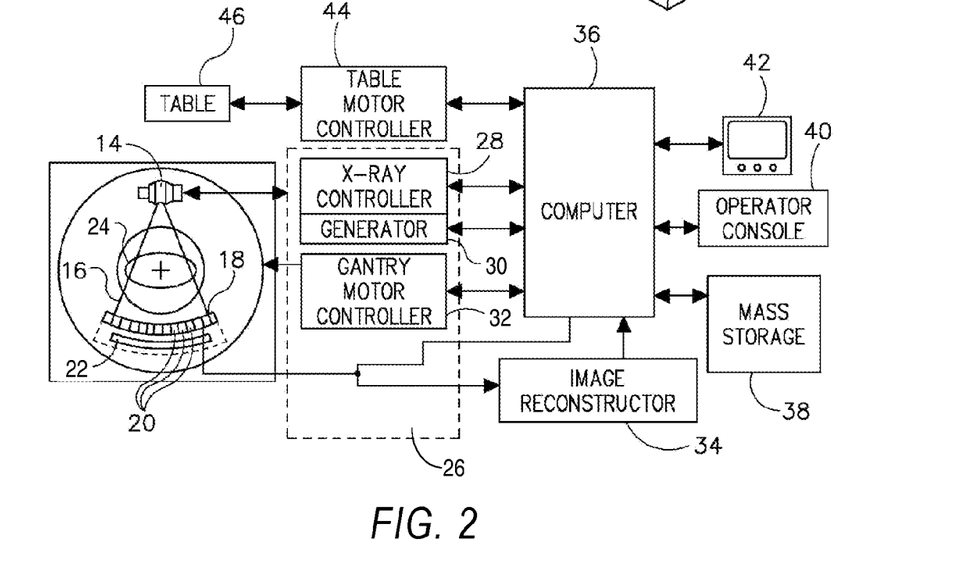
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
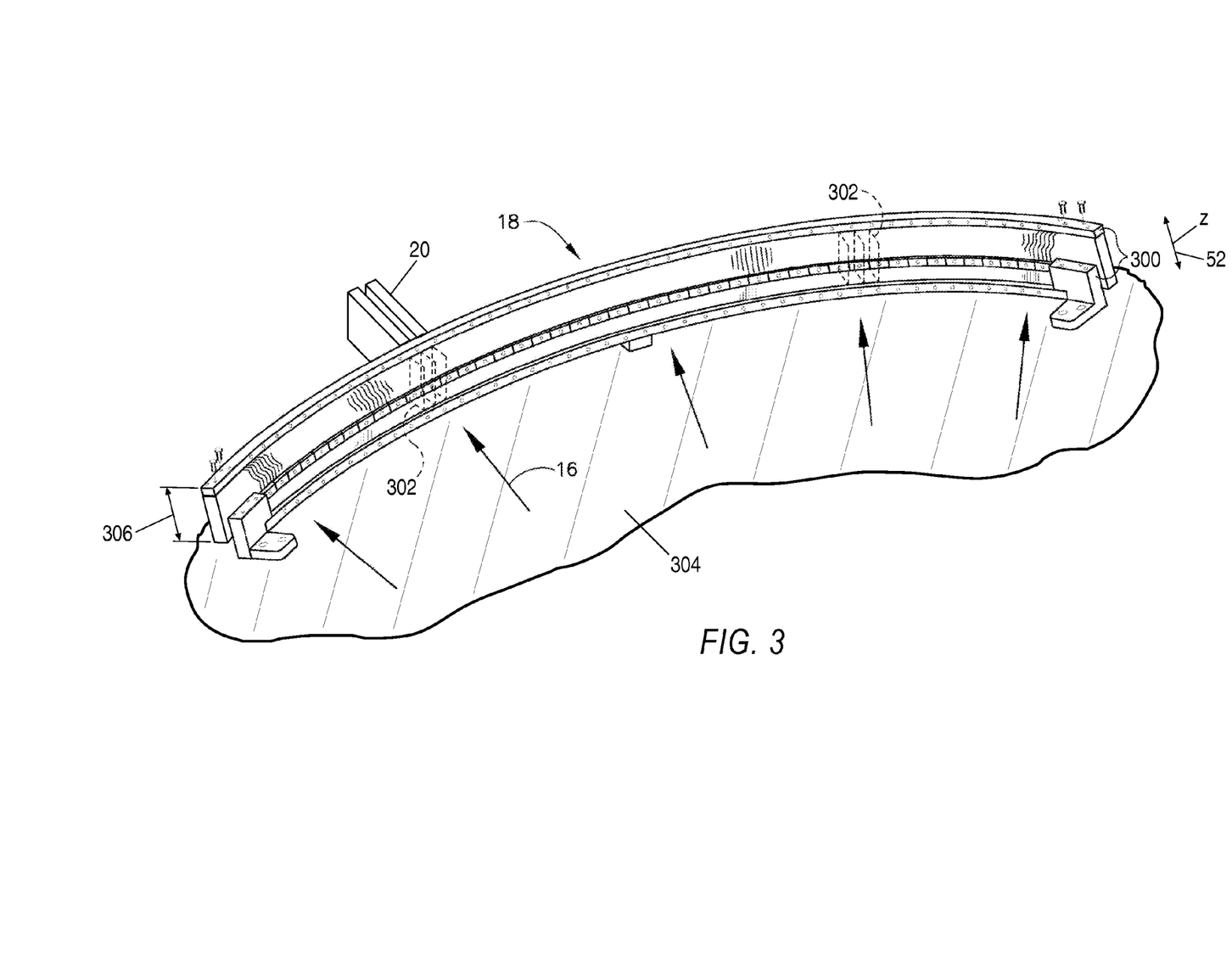
FIG. 3 is a perspective view of one embodiment of a CT system detector array.

As shown in FIG. 3, a typical detector assembly 18 includes rails 300 having collimating blades or plates 302 placed therebetween. Plates 302 are positioned to collimate x-rays 16 before such beams impinge upon, for instance, detector 20 of FIG. 4 positioned on detector assembly 18. In one embodiment, detector assembly 18 includes fifty-seven detectors or detector modules 20, each detector 20 having an array size of 64×16 of pixel elements 400. As a result, detector assembly 18 has sixty-four rows and nine hundred twelve columns (16×57 detectors) which allows sixty-four simultaneous slices of data to be collected with each rotation of gantry 12. Rails 300 are mounted to a plate 304 that is vertically mounted in gantry 12. Z-axis 52 therefore extends orthogonal to plate 304 such that rails 300 extend axially and at a distance 306 from plate 304. Thus, as detectors grow in z-direction 52, so too does cantilever distance 306.

Figure 4:
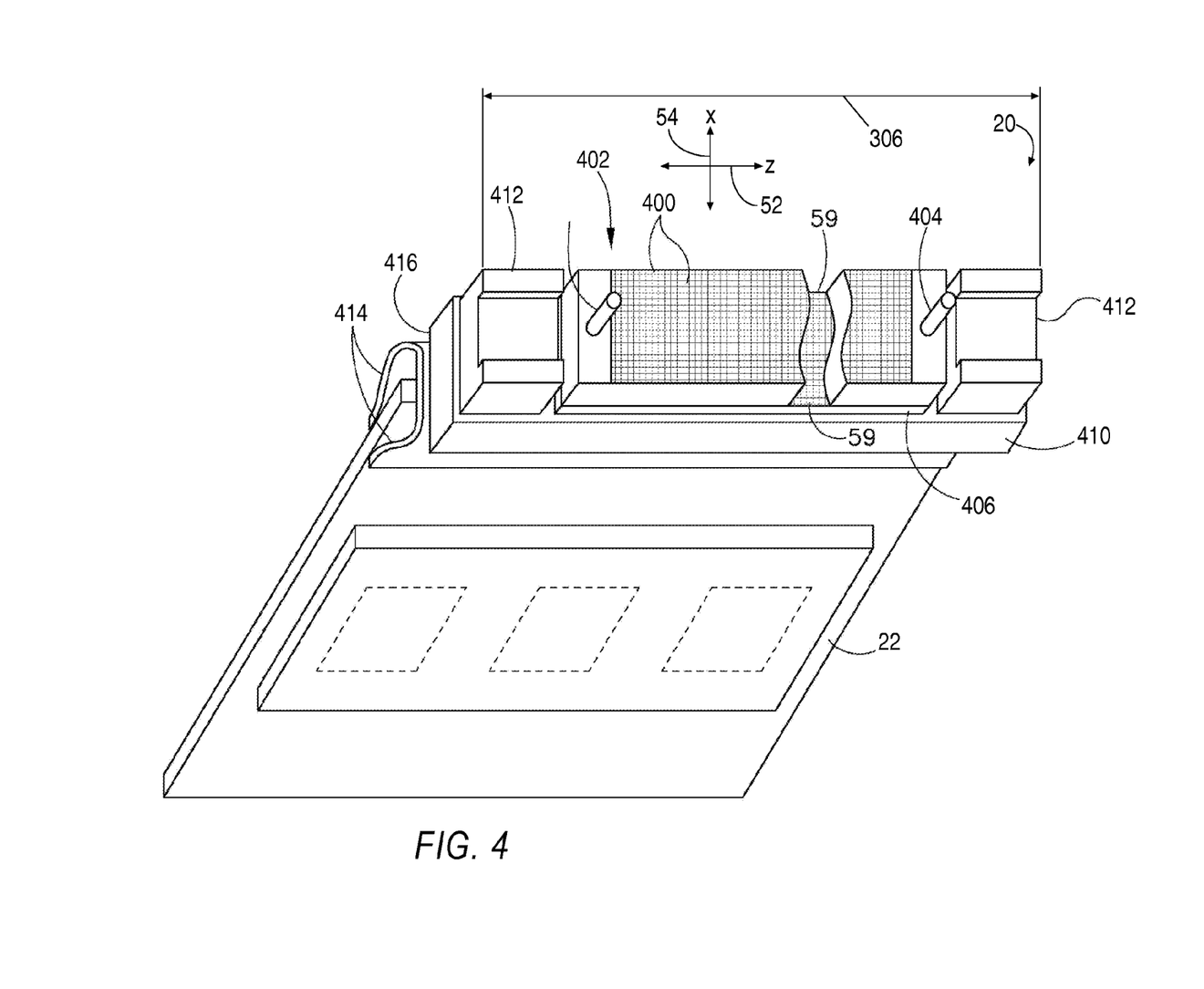
FIG. 4 is a perspective view of one embodiment of a detector.

Referring to FIG. 4, detector 20 includes DAS 22, with each detector 20 including a number of detector elements 400 arranged in pack 402, and having a width 306 that corresponds to the cantilever length 306 shown in FIG. 3. Detectors 20 include pins 404 positioned within pack 402 relative to detector elements 400. Pack 402 is positioned on a backlit diode array 406 having a plurality of diodes 408. Backlit diode array 406 is in turn positioned on multi-layer substrate 410. Spacers 412 are positioned on multi-layer substrate 410. Detector elements 400 are optically coupled to backlit diode array 406, and backlit diode array 406 is in turn electrically coupled to multi-layer substrate 410. Flex circuits 414 are attached to face 416 of multi-layer substrate 410 and to DAS 22. Detectors 20 are positioned within detector assembly 18 by use of pins 404.

Figure 5A:
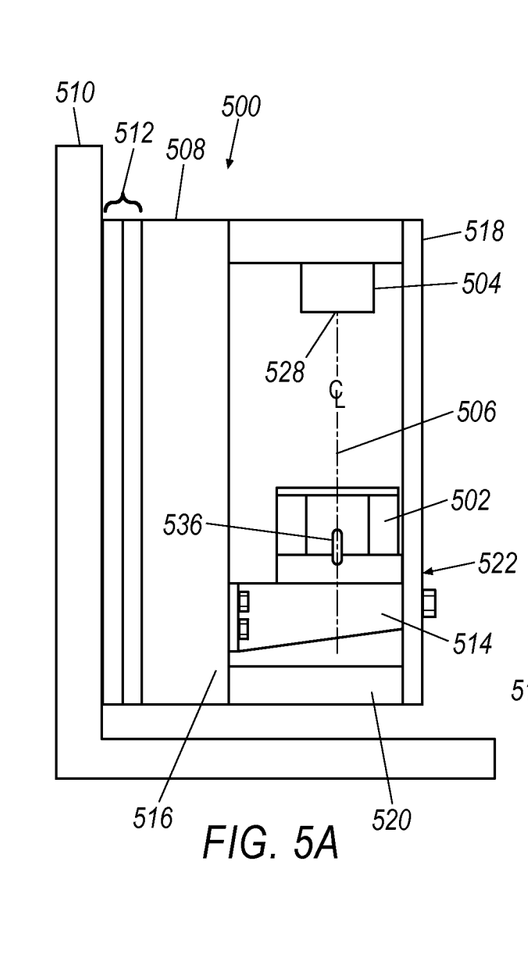
FIGS. 5A and 5B are side and plan views of a detector assembly in a gantry, according to an embodiment.
Figure 5B:
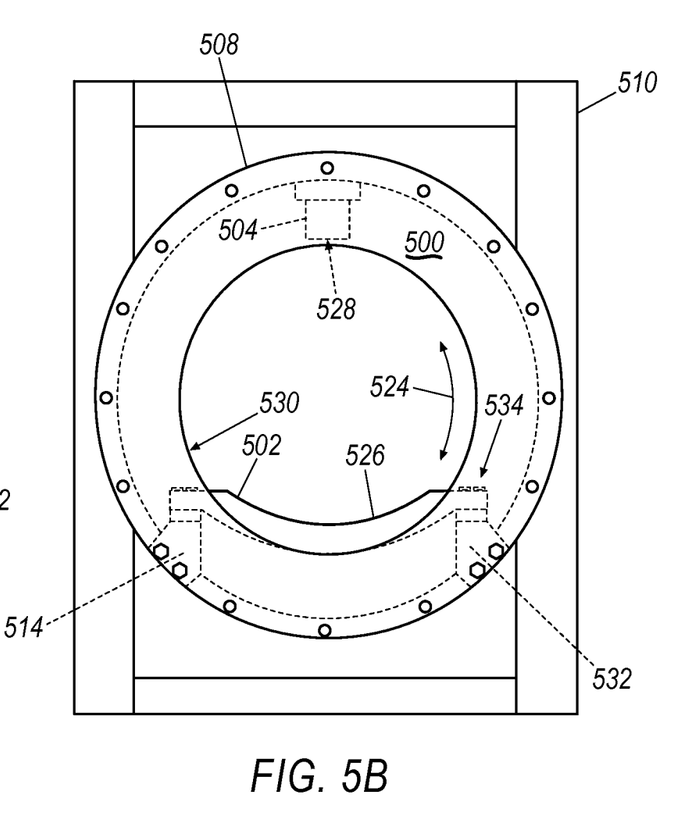

Referring to FIGS. 5A and 5B, side and plan views of a gantry are shown, according to embodiments, which may be incorporated into system 10 of FIGS. 1 and 2. Gantry 500 includes an arc-shaped or arcuate structure or detector assembly 502 and x-ray tube 504 that are coupled or mounted axially with respect to one another such that a centerline 506 of x-ray tube 504 corresponds with a center of detector assembly 502. Gantry 500 includes a rotatable base 508 positioned on or coupled to a stationary base 510, and having a bearing 512 mounted therebetween. Detector assembly 502 includes a plurality of detectors, as shown in FIGS. 3 and 4, which are positioned to receive x-rays that are generated by x-ray tube 504 and pass through an object, such as object 24 of FIG. 1. The detectors are positioned at approximately the same distance from a focal spot 528 of x-ray source 504. A support frame 514 is attached to rotatable base 508 at a first axial location 516. A support structure 518 such as a face plate is attached to rotatable base 508 via an axial extension support or drum 520 which, as one example, is a generally cylindrical shaped support structure and positioned radially external to support frame 514. Support frame 514 is thereby supported by support structure 518 at a second axial location 522. As such, detector assembly 502 is straddle mounted and supported on both axial locations 516, 522.

Detector assembly 502 extends along a generally circumferential direction 524 and includes a surface 526 that is approximately radially equidistant from focal spot 528 of x-ray tube 504. X-ray tube 504 is positioned to generate x-rays toward detectors (not shown) mounted on surface 526, and x-ray tube 504 is attached to axial extension support 520. Support frame 514 is attached to rotatable base 508 at first axial location 516 and second axial location 522. Support frame 514 is also attached to rotatable base 516 at a first circumferential end 530 of arcuate structure 502. A second support frame 532 is attached to rotatable based 508 at a second circumferential end 534 of arcuate structure 502. According to one embodiment, a locating pin 536 provides positioning location or restraint for detector assembly 502 with respect to support frame 514. Slots or holes may be positioned in each component 502, 514 such that accurate axial positioning is achieved. As such, detector assembly 502 may be positioned axially in a very accurate fashion with respect to x-ray tube 504 and particularly with respect to focal spot 528.

According to one embodiment, an electrically resistive and/or thermally insulating material is positioned between the rotating and stationary components of gantry 500. For instance, one or both of components of bearing 512 may be fabricated from a ceramic, or an intermediate plate (not shown) may be included. In such fashion a joint between rotating and stationary components can be maintained in compression (ceramics tend to have good compression properties), having both desired electrical and thermal properties. Thus, stray heat flow from the gantry to the base is reduced, providing better thermal control in components of detector assembly 502. Electrical isolation as well can be used to advantage to isolate components of detector assembly 502 from, for instance, noisy chassis ground and the like. Further, although components of bearing 512 have been described as thermally and electrically isolating, it is contemplated that insulating materials may be placed elsewhere, such as at the mount joint at first axial location 516.

Thus, the straddle mount detector solves at least two historic issues with traditional cantilever designed detectors. The first has to do with detector deflection, in which cantilever designs tend to exhibit roll about the channel (or x) direction. Roll results in image artifacts if it is excessive and leads to a great deal of structural design issues. The second issue solved is one of scalability since the tube and detector center line 506 is collinear. Further, when changing from one size detector coverage on a given gantry, as the detector coverage increases (detector width along a z or patient axis of the gantry, such as z-axis 52 shown in FIG. 1) the x-ray tube 504 is offset to maintain alignment with detector center. Extending in a direction of z-axis 52 also causes a shift in center of gravity (CG) of both the x-ray tube and detector assembly. By straddle mounting and central pinning the tube and detector, centerlines remain fixed as does the CG of the detector, simplifying scalability to larger z-coverage and reducing time in developing next generation detectors.

Figure 6:
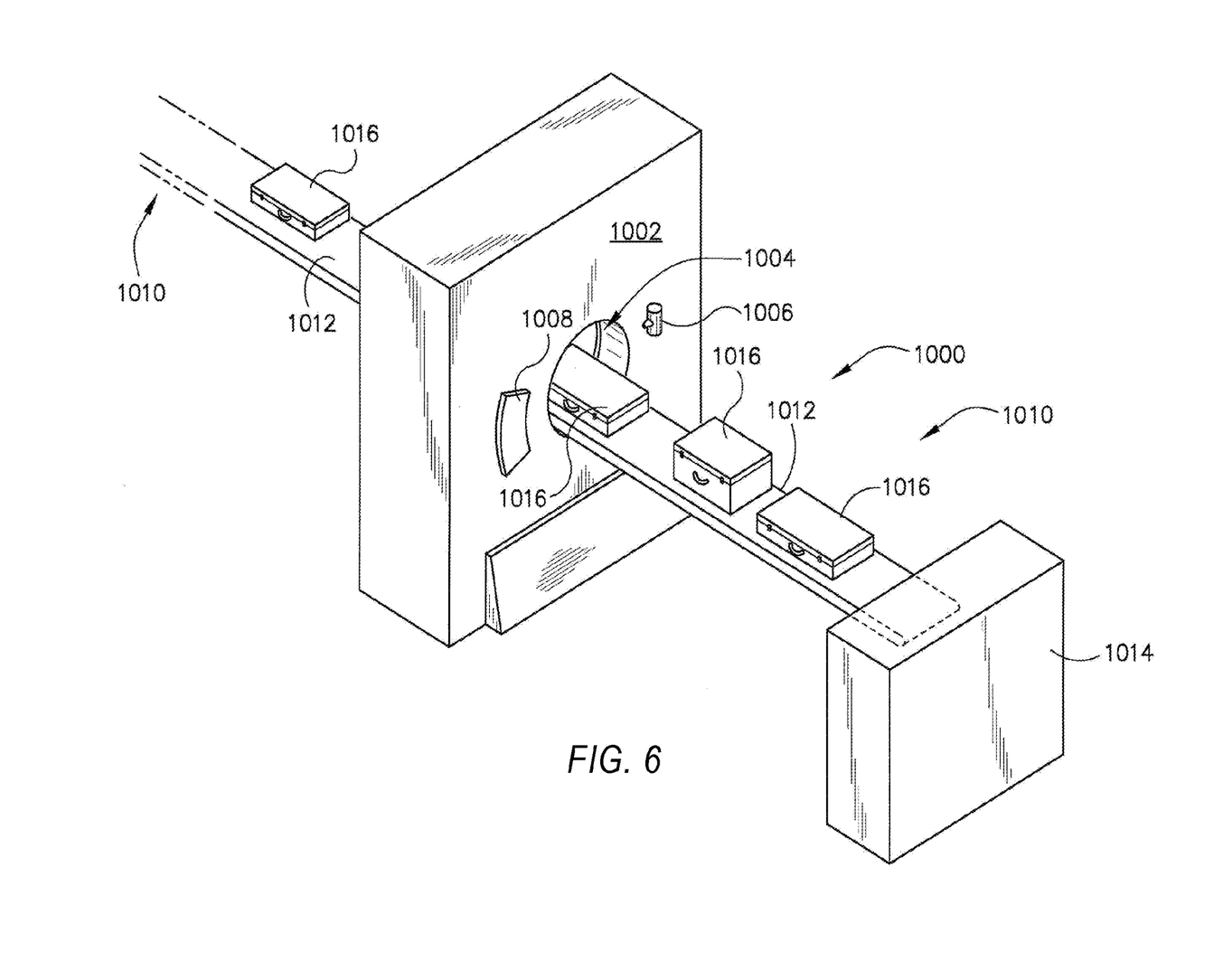
FIG. 6 is a pictorial view of a CT system for use with a non-invasive package inspection system according to an embodiment.

Referring now to FIG. 6, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes a gantry having a rotatable base and having an opening for receiving an object to be scanned, and a detector assembly. The detector assembly includes a plurality of detectors positioned to receive x-rays having passed through the object, and an arcuate structure positioned to support the plurality of detectors. A first support frame is attached to the rotatable base at a first axial location and supported at a second axial location, wherein the arcuate structure is attached to the first support frame between the first axial location and the second axial location.

According to another embodiment, a method of assembling a CT system includes coupling a rotatable base to a gantry, the gantry having an opening for receiving an object to be scanned, attaching an arc-shaped structure to the rotatable base via a first support frame such that the arc-shaped structure is supported at a first axial location and a second axial location, and positioning a plurality of detectors on a surface of the arc-shaped structure to receive x-rays that pass through the opening and through the object.

According to yet another embodiment, a detector assembly for a CT imaging system includes an arced structure having a plurality of detectors positioned thereon, wherein the assembly is attachable to a rotatable base of the CT system such that x-rays generated in the imaging system impinge upon the plurality of detectors after having passed through an object to be imaged, and a first support frame that axially straddles the arced structure and supports the arced surface at a first axial location and a second axial location.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosed subject matter is not limited to such disclosed embodiments. Rather, that disclosed can be modified to incorporate any number of variations, alterations, substitutions or equivalent arrangements not heretofore described, but which are commensurate with the spirit and scope of the disclosed subject matter. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
    a gantry having a rotatable base and having an opening for receiving an object to be scanned;
    a detector assembly comprising:
        a plurality of detectors positioned to receive x-rays having passed through the object; and
        an arcuate structure positioned to support the plurality of detectors, the arcuate structure extending along a generally circumferential direction of the gantry and having a surface that is approximately radially equidistant from a focal spot of an x-ray tube that is coupled to the rotatable base;
    a first support frame attached to the rotatable base at a first axial location and supported at a second axial location, wherein the arcuate structure is attached to the first support frame between the first axial location and the second axial location; and
    wherein the arcuate structure is mounted to the gantry via a locating pin that positions the arcuate structure along an axial direction of the gantry.

2. The CT system of claim 1, further comprising a face plate attached to the rotatable base, and attached to the first support frame at the second axial location to provide the support at the second axial location.

3. The CT system of claim 2, further comprising an axial extension support that is positioned between the rotatable base and the face plate, and also positioned radially external to the first support frame.

4. The CT system of claim 3, wherein the axial extension support is a generally cylindrical shape.

5. The CT system of claim 3, wherein the x-ray tube is positioned to generate the x-rays toward the plurality of detectors, and wherein the x-ray tube is attached to the axial extension support.

6. The CT system of claim 1, further comprising a second support frame attached to the rotatable base at the first axial location and the second axial location, wherein the first support frame is attached to the rotatable base at a first circumferential end of the arcuate structure, and the second support frame is attached to the rotatable based at a second circumferential end of the arcuate structure.

7. The CT system of claim 1, further comprising an insulating material positioned between the first support frame and the rotatable base.

8. The CT system of claim 1, wherein the locating pin is positioned in the x-direction.

9. A method of assembling a CT system, comprising:
    coupling a rotatable base to a gantry, the gantry having an opening for receiving an object to be scanned;
    attaching an arc-shaped structure to the rotatable base via a first support frame such that the arc-shaped structure is supported at a first axial location and a second axial location;
    attaching a face plate to the rotatable base and to the first support frame at the second axial location to provide support to the arc-shaped structure;
    attaching a cylindrical axial extension support between the rotatable base and the face plate;
    attaching an x-ray source to the rotatable base via the cylindrical axial extension support; and
    positioning a plurality of detectors on a surface of the arc-shaped structure to receive x-rays that pass through the opening and through the object.

10. The method of claim 9,
    wherein the arc-shaped structure includes a surface on which the plurality of detectors is positioned, such that each of the plurality of detectors is positioned at approximately the same distance from a focal spot of the x-ray source.

11. The method of claim 9, further comprising attaching a second support frame to the rotatable base at the first axial location and the second axial location, wherein the first support frame is attached to the rotatable base at a first circumferential end of the arc-shaped structure, and the second support frame is attached to the rotatable based at a second circumferential end of the arc-shaped structure.

12. The method of claim 9, further comprising coupling the rotatable base to the gantry via a gantry bearing.

13. A detector assembly for a CT imaging system, the assembly comprising:
   an arced structure having a plurality of detectors positioned thereon, wherein the assembly is attachable to a rotatable base of the CT system such that x-rays generated in the imaging system impinge upon the plurality of detectors after having passed through an object to be imaged;
   a first support frame that axially straddles the arced structure and supports the arced surface at a first axial location and a second axial location; and
   wherein the arced structure extends along a circumferential direction of the rotatable base to which the assembly is attachable, and wherein the arced structure includes a pin locating feature for locating the detector assembly to the rotatable base along an axial direction of the CT imaging system.

14. The detector assembly of claim 13, wherein the arced structure includes a surface that is approximately radially equidistant from a focal spot of an x-ray tube that is coupled to the rotatable base to which the assembly is attachable.

15. The detector assembly of claim 13, wherein the detector assembly is attachable to a face plate that is attached to the rotatable base.

16. The detector assembly of claim 13, wherein the face plate is attached to the first support frame at the second axial location to provide the support at the second axial location.

17. The detector assembly of claim 13, wherein the pin locating feature is positioned in the x-direction.

* * * * *